US007445889B2

(12) United States Patent
Smith-Norowitz et al.

(10) Patent No.: US 7,445,889 B2
(45) Date of Patent: Nov. 4, 2008

(54) METHODS FOR DETECTING PARVOVIRUS INFECTIONS

(75) Inventors: Tamar Smith-Norowitz, Brooklyn, NY (US); Kevin D. Norowitz, Brooklyn, NY (US); Martin H. Bluth, West Hempstead, NY (US); Helen G. Durkin, Manhasset, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 10/555,958

(22) PCT Filed: May 5, 2004

(86) PCT No.: PCT/US2004/014012

§ 371 (c)(1),
(2), (4) Date: Nov. 28, 2006

(87) PCT Pub. No.: WO2004/098391

PCT Pub. Date: Nov. 18, 2004

(65) Prior Publication Data

US 2007/0166823 A1      Jul. 19, 2007

Related U.S. Application Data

(60) Provisional application No. 60/467,855, filed on May 5, 2003.

(51) Int. Cl.
*C12Q 1/70*     (2006.01)
*G01N 33/00*    (2006.01)
*G01N 33/53*    (2006.01)
*C12N 7/00*     (2006.01)

(52) U.S. Cl. .................... 435/5; 435/7.1; 435/7.92; 435/235.1

(58) Field of Classification Search .................. None
See application file for complete search history.

(56) References Cited

OTHER PUBLICATIONS

Campoy, et al. Seroprevalence of B19 infection in patients with acute polyarthritis. Rev. Clin. Esp. 1996; 196(12)828-30. [Abstract Only].*
Sun, et al. Transfectomas Expressing Both Secreted and Membrane-Bound Forms of Chimeric IgE With Anti-Viral Specificity. The Journal of Immunology. 1991; 146(1):199-205.*
Bluth M.H. et al., "Detection of IgE Anti-Parvovirus B19 and Increased CD23+ B Cells in Parvovirus B19 Infection: Relation to $Th_2$ Cytokines", *Clinical Immunology*, 108(2):152-158 (2003).
Forsgren L.G. et al., "Influence of Maternal Infections with Viral Agents or *Toxoplasma Gondii* During Pregnancy on Fetal IgE Production", *Allergy*, 52(10):978-984 (1997).
Reolid E.C. et al., "Seroprevalencia De La Infección Por Parvovirus B19 En Pacientes Afectos De Poliartritis Aguda", *Revista Clinica Espanola*, 196(12):828-830 (1996).
Biasi D. et al., "A Case of Parvovirus-B19 Adult Acute Arthritis with Some Allergic Disease Clinical Features", *Clinical Rheumatology*, 15(5):508-510 (1996).

* cited by examiner

*Primary Examiner*—Mary E. Mosher
*Assistant Examiner*—Stuart W Snyder
(74) *Attorney, Agent, or Firm*—Scully, Scott, Murphy & Presser, P.C.

(57) ABSTRACT

The present invention provides a method for diagnosing a subject suffering a pathological condition characterized by parvovirus infection by detecting the presence of IgE anti-Parvovirus B 19 antibodies.

11 Claims, 2 Drawing Sheets

METHODS FOR DETECTING PARVOVIRUS INFECTIONS

CROSS REFERENCE TO RELATED APPICATION

The present application claims benefit of U.S. Provisional Application No. 60/467,855 filed on May 5, 2003.

FIELD OF THE INVENTION

The present invention generally relates to methods useful for diagnosis and prognosis of parvovirus infected patients by detecting the presence of IgE anti-Parvovirus B19 antibodies. The present invention provides antibody-based compositions, methods and combined protocols for treating viral infections, including Parvovirus B19 infection and other viral infections. An immunologic composition is also provided.

BACKGROUND OF THE INVENTION

Parvoviruses are small, DNA-containing viruses that infect a variety of animal species. Several parvoviruses are recognized as important causes of disease in animals such as canine parvovirus and feline panleukopenia virus, but parvovirus B19 is the only strain that is pathogenic in humans. Parvovirus B19 is a member of the genus Parvovirus in the family Parvoviridae. The mammalian parvoviruses are very species specific. B19 does not infect other animals, and animal parvoviruses do not infect humans. Human Parvovirus B19 occurs endemically worldwide. It causes epidemics in small areas, especially affecting kindergartens and schools. Parvovirus B19 infection is generally a self-limiting childhood disease. For example, it was proved that Parvovirus B19 to be the cause of a benign self-limiting childhood exanthema (fifth disease or erythema infectiosum (EI)). However, infection with parvovirus can be dangerous, for example, causing aplastic anemia and/or fetal death in certain groups, e.g., patients with sickle cell anemia. Persistent Parvovirus B19 infection can also cause chronic arthropathies. In immunodeficient patients, parvovirus infection can result in chronic anemia Parvovirus B19 is also an important cause of nonimmune hydrops fetalis. (Hibbs J. and Young N., *Infectious Diseases* 912 (Hoeprich D. et al. eds., J. B. Loppincon Co., Philadelphia, 5th ed. 1994)). There may also be a direct effect of the virus on myocardial tissue (Nelson's Textbook of Pediatrics 15$^{th}$ Ed. 1996).

Laboratory tests for the diagnosis of B19 infection are not available routinely. Diagnosis of EI is usually based on clinical observation of the typical rash and exclusion of other conditions. The virus cannot be isolated by culture. In evaluation of suspected Parvovirus B19 infections, a complete blood cell count and blood chemistry profile are useful in addition to thorough history taking and physical examination (Marshal et al., *Postgraduate medicine.* 95(8): 165-168, 1994). However, diagnosis of acute and past infection of Parvovirus B19 is based on detection of IgM and IgG antibodies (Pickering et al., *Clin. and Diag. Virol.* 9(1): 57-63, 1998). Studies of Cassinotti, et al. demonstrated the prevalence of IgG anti-Parvovirus B19 antibodies in patients with various forms of arthritis (Cassinoti et al., *Annals of Rheumatic Disease.* 54(6): 498-500, 1995). Others have studied the serological profiles and/or prevalence for human Parvovirus B19 in patients with fibromyalgia (FM) (Branco et al., *Infeccao viral e fibromialgia.* 7(6): 337-341, 1994), AIDS, and other infections (Mudde et al., *Allergy.* 50:193-199, 1995). Recombinant versions of Parvovirus B19 viral capsid proteins VP1 and VP2 have been used as antigens for immunodiagnostic assays, including either IgM or IgG enzyme immunoassays (EIA), immunofluorescence assays (IPA), or Western blot assays, for detection of antiviral antibodies (Kerr et al., *J Med Virol.* 57(2): 179-185, 1999).

IgE antibodies have been identified in studies of virus other than parvovirus, e.g., IgE anti-parainfluenza virus (Welliver et al., *J. Pediatrics.* 101(6): 889-896, 1982) and IgE anti-respiratory syncytial virus (RSV) (Welliver et al., *New England J of Med.* 305(15): 841-846, 1981; Russi et al., *J Clin. MicrobioL* 31: 819-823, 1993) in sera from pediatric patients (Welliver et al., 1982). However, IgE anti-RSV-F(a) and IgE anti-RSV-G(a) antibodies were not detected in nasal washes and sera from infants (De Alarcon et al., *J Pediatrics.* 138(3): 311-7, 2001).

Previous studies have also identified the presence and function of IgE anti-HIV antibodies in the serum of a subset of HIV-1 seropositive, nonprogressor pediatric patients, who remained relatively healthy, despite decreased numbers of peripheral blood CD4+T cells (Secord et al., *J Allergy Clin Immunol.* 98(5): 979-984, 1996; Pellegrino et al., *AIDS Research and Human Retroviruses* 18(5):367-76, 2002).

It is well known that immunological factors play an important role in virus pathogenesis (Clerici et al., *Immunol. Today.* 107: 14-20, 1993). For example, patients chronically infected with Hepatitis C Virus (HCV) exhibit immune dysfunction with a Th2-dominant cytokine profile, while Th1 cytokines are prominent in those with self-limited HCV infection (Sauerbruch et al., *C. J. Hepatol.* 31: 971-976, 1999; Tsai et al., *Hepatology.* 25: 449-457, 1997). Both Thl and cytotoxic T lymphocyte ("CTL") responses have been reported to play a crucial role in recovery from HCV infection (Missale et al., *J. Clin. Invest.* 98: 706-715, 1996; Chang et al., *C. J. Immunol.* 162: 1156-1163, 1999). Furthermore, in HIV-1 disease, the loss of the Th1 response has been correlated with disease progression and loss of protective cellular immunity (Walker et al., *AIDS.* 4: 177-184, 1990). Similar studies, in HIV-1 disease, have shown a persistence of HIV-1 specific IgE after 210 days, and retained its ability to suppress HIV-1 production in vitro (Pellegrino et al.). Further, it has been demonstrated that specific IgE anti-HIV-1 antibodies can protect a subject against HIV-1 disease progression by promoting cytotoxic responses or by suppressing virus production (Secord et al.; Pellegrino et al.; Seroogy et al., *J. All. Clin. Immunol.* 104: 1045-1051, 1999).

It was demonstrated that the low affinity receptor for IgE, CD23, can be proteolytically cleaved from surfaces of CD23 expressing cells into biologically active soluble fragments, some of which retain the ability to bind IgE (Dugas et al., *Euro. Cytokine Network.* 3: 35-41, 1992). It has also been shown that CD23 (membrane bound and soluble forms) increases production of IgE by B cells through interacting with CD21 on B cell surfaces (Bonnefoy et al., *Int. Arch Allergy Immunol.* 104: 40-42, 1995; Bonnefoy et al., *Immunol. Today.* 12: 418420, 1996). The increase in CD23 may also serve to regulate selective IgE responses. See, e.g., Delespesse et al., Immunol. Rev. 125: 77-97, 1992, as well as provide an initial anti-viral response, as demonstrated in parasitic infection. See, e.g., Capron et al., Science. 264: 1876-1877,1994; Vouldoukis et al., Proc. Natl. Acad. Sci. 92: 7804-7808, 1995.

Functions of CD23 include specific regulation of IgE production, IgE-mediated cytotoxicity and release of mediators, IgE-dependent antigen focusing, and promotion of B cell growth (Fujiwara et al., *Proc Nat. Acad. Sci USA.* 91(15): 6835-6839, 1994). CD23 has also been shown to increase on monocytes in AIDS (Miller et al., *AIDS Research and Human*

*Retroviruses* 17:443-52, 2001). In addition, CD23+ expression by peripheral blood leukocytes ("PBL") has been evaluated in diseases such as rheumatoid arthritis (RA) (Fernandez-Gutierrez et al., *Clin Immunol Immunopathol.* 72(3): 321-327, 1994) and HV-1 (Larcher et al, *J Acq. Immune Def Syn.* 3: 103-108, 1990). However, later studies found decreased numbers of CD23+ B cells (Larcher et al; Rodriguez et al., *Clin. Immunol and Immunopath.* 81: 191-199, 1996), and increased numbers of CD23+ T cells (Carini et al., *Proc. Nat. Acad. Sci. USA* 85: 9214-9218, 1988; Carini et al., *Int Arch. Allergy Appl. Immunol.* 88: 116-118, 1989) in HIV-1.

Further, studies of Imani, et al., have shown that infection with MMR vaccine can induce IgE class switching in a human B cell line and freshly prepared PBL (Imani et al., *Clin. Immunol.* 100(3): 355-61,2001). It has also been implicated that an IgE bounds to its Fc receptor as an (APC) Antigen Presenting Cell in atopy (Mudde et al.).

Previous serology studies, through ELISA methodology, have identified IgM (in early stage of infection) and IgG (chronic presence in a patient) antibodies, but not IgE antibodies, specific against Parvovirus B19 antigens. Moreover, the level of total IgG or IgM in healthy people and in parvovirus infected patients does not have diagnostically significant difference. Therefore, an immunoglobulin specific for Parvovirus B19, such as an antibody, which is only detectable in parvovirus infected patients but not detectable in healthy people, would have diagnostic and/or prognostic implications to facilitate the early detection of parvoviral infection thereby permitting early intervention to treat or prevent the deleterious effects of Parvovirus infection.

SUMMARY OF THE INVENTION

One embodiment of the present invention is directed to a method for diagnosing a subject suffering a pathological condition associated with or resulting from or caused by parvovirus infections by detecting the presence of IgE anti-Parvovirus B19 antibodies.

In one aspect of the present invention, the detection of IgE anti-Parvovirus B19 antibodies permits the prognosis of a subject having a parvovirus infection, particularly Parvovirus B19 infection, by stratifying the subject, particularly based on signs, symptoms, severity, duration, co-morbid factors, and long-term sequelae of the infection, more particularly, by directing treatment options for the subject.

In another aspect of the present invention, antigen specific IgE antibodies can be determined with a greater sensitivity by the detection method described herein. The detection method of the present invention provides a greater degree of sensitivity than conventional serology.

A test kit for diagnosing parvovirus infection is a further aspect of the present invention.

Another embodiment of the present invention is directed to a substantially pure IgE anti-viral antibody, e.g., IgE anti-Parvovirus B19 antibodies.

One aspect of the present application is directed to IgE anti-Parvovirus B19 monoclonal antibodies or humanized antibodies or human antibodies, especially substantially pure antibodies thereof.

Hybridoma cell lines which produce IgE anti-Parvovirus B19 form another embodiment of the present invention.

Another aspect of the present invention is directed to functional derivatives of the monoclonal or humanized antibodies of the present invention.

A further aspect of the invention is directed to pharmaceutical compositions which comprise a therapeutically effective amount an IgE anti-Parvovirus B19 antibody of the present invention, or a functional derivative thereof, or combinations thereof and a pharmaceutical carrier therefor.

The pharmaceutical compositions of the present invention can also include other substances such as cytokines, adjuvants and pharmaceutically acceptable carriers.

A further embodiment of the present invention is directed to methods of treating a subject suffering a pathological condition characterized by parvovirus infection. In accordance with the present invention, the subject is treated by administering a therapeutically effective amount of pharmaceutical compositions of the present invention as defined herein.

Pathological conditions which can be diagnosed and/or treated by practicing the present invention include, but not limited to, parvovirus infection associated aplastic anemia, chronic arthropathies, chronic anemia and cardiomyopathies.

Dosages and routes of the administration of an antibody are also contemplated by the present invention.

An even further aspect of the present invention provides an immunogenic composition suitable for administration to a human, comprising an immunogenically effective amount of Parvovirus B19 antigens or Parvovirus antigen subfragments or mixtures thereof and a pharmaceutically acceptable diluent.

DETAILED DESCRIPTION OF THE INVENTION

Figure 1:
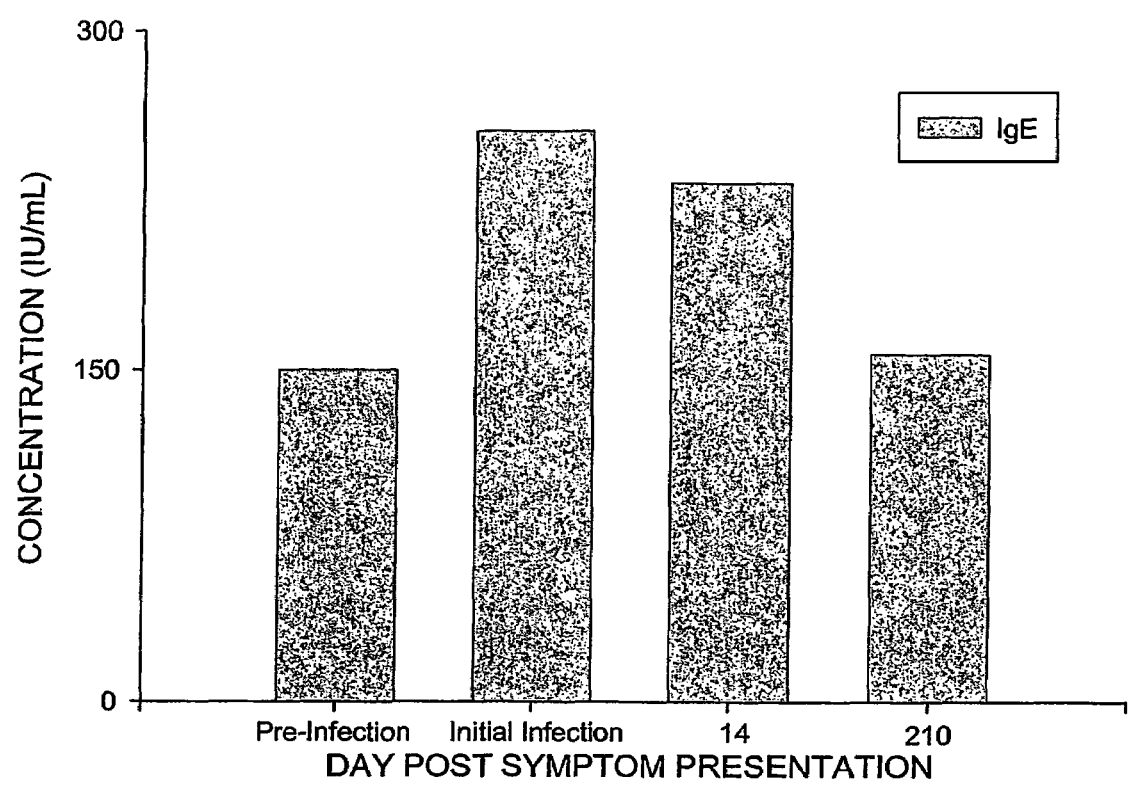
FIG. 1 depicts immunoglobulin levels in the serum of a Parvovirus B19 patient. Total serum IgE levels were determined (Total IgE Fluoroenzymeimmuinoassay) pre-infection, and on day 0 (initial infection), and days 14 to 210 post symptom presentation ("psp"), in serum of a Parvovirus B19 patient. Data are expressed as IU/ml.

According to an embodiment of the present invention, the inventors have discovered the presence of IgE anti-Parvovirus B19 antibodies in serum obtained from Parvovirus B19 infected patients, including children. Specifically, the present inventors have detected IgE anti-Parvovirus B19 antibodies in serum of a patient on day 0 (initial presentation) and their persistence 7 months post symptom presentation ("psp"). By "day 0" is meant that patient is initially diagnosed as Parvovirus B19 infected, as determined by the presence of, e.g., "slap cheek" rash, IgG and IgM anti-Parvovirus B19 antibodies in serum.

Accordingly, the present invention provides that the presence of IgE anti-Parvovirus B19 antibodies is useful in diagnosis and treatment of Parvovirus B19 infections. More specifically, the present inventors have discovered that an IgE anti-Parvovirus B19 antibody can identify any of the Parvovirus B19 antigens (NS-1, VP-1, VP-2) or antigen subfragments (VP-1S, VP-N, VP-C) by employing a method, such as the Western blot method. The Parvovirus B19 antigens and the antigen subfragments used in the present invention are obtained through genetic engineering of the nonstructural protein (NS-1), the two capsid proteins (VP-1 and VP-2), N-terminal half of VP-1 and VP-2 proteins (VP-N), C-terminal half of VP-1 and VP-2 proteins (VP-C) and specific segment of VP-1 protein (VP-1S) of human Parvovirus B19. The method of the present invention permits identification of these viral antigens and antigen subfragments with a greater sensitivity than conventional methods, such as the ELISA method used in previous studies (in general, up to two orders of magnitude of increased resolution).

Moreover, the method of the present invention is also useful for identifying and stratifying patients, who will progress with sequelae, as well as directing future treatment options. Furthermore, the inventors have demonstrated that IgE anti-Parvovirus B19 antibodies involve a significant role in anti-viral immunity and that there occurs a cytokine pattern switch, from a Th2 predominant patter to a Thl and Th2 prevalent pattern, during parvovirus infection. Accordingly, the present invention provides methods for treating pathological conditions associated with parvovirus infections, using IgE anti-Parvovirus B19 antibodies, preferably coupled with one or more cytokines, such as Thl and/or Th2 type cytokines.

In accordance to the present invention, (1) IgE anti-Parvovirus B19 antibodies are produced by Parvovirus B19 infected subjects including children, and are useful for diagnosis, prognosis and treatment of parvovirus infections; (2) Th2 cytokine responses predominate early in IgE anti-Parvovirus B19 infection, whereas late in Parvovirus B19 infection Thl and Th2 cytokine responses both are prevalent; (3) CD23 surface expression on B cells is increased on peripheral blood lymphocytes from Parvovirus B19 infected subjects. Therefore, the present invention contemplates immunogenic compositions and vaccines comprising parvovirus antigens for the prevention of parvovirus infections.

Another embodiment of the present invention is directed to a method for diagnosing a subject suffering a pathological condition associated with, or caused by or resulting from a viral infection by detecting the presence of IgE antiviral antibodies. For example, in this embodiment, the present invention is directed to a method for diagnosing a subject suffering a pathological condition caused by, resulting from or associated with a parvovirus infection by detecting the presence of IgE anti-Parvovirus B19 antibodies in a biological sample from the subject. The following technique is exemplary with respect to IgE anti-Parvovirus antibodies, but is applicable for the detection of other IgE antiviral antibodies.

According to the present invention, IgE anti-Parvovirus antibodies can be detected from a biological sample, such as plasma, peripheral blood, urine, sputum/saliva, or serum, of a subject infected by parvovirus, particularly Parvovirus B19, using any well established method in the art, such as enzyme-linked immunosorbent assay (ELISA), nucleic acid and testing, western blot and the like. In one example of the present invention, a test strip (Mikrogen, Martinsried, Germany) is loaded with Parvovirus B19 antigens or antigen subfragments and is incubated with a biological sample. Preferred antigens include NS-1, VP-1 or VP-2, or mixtures thereof Preferred antigen subfragments include VP-1S, VP-N or VP-C, or mixtures thereof More preferably, a mixture of both Parvovirus B19 antigens and antigen subfragments is used. Even more preferably, a test strip loaded with all of VP-1, VP-2, NS-1, VP 1-S, VP-N and VP-C is used. Preferred biological samples include plasma, peripheral blood, urine or serum from a subject. A particularly preferred sample is serum.

In accordance with the present invention, the sera from a subject is diluted, preferably 1:100, in washing/diluting buffer (Tris-buffered saline, NaCl, TWEEN 20(polyoxyethylene-20-sorbitan Monolaurate) 0.01% MIT, 0.1% oxypyrin, protein). The test strip is incubated with the sample in a container, e.g., a dish, shaking for a sufficient time, preferably, 10-20 hours, more preferably, 20 hours, at room temperature. The strips are washed several times, e.g., four times, in washing/diluting buffer. Polyclonal anti-IgE antibodies, preferably, goat polyclonal anti-human IgE antibodies (ICN Biomedicals, Aurora, Ohio), diluted, preferably 1:50 or 1:100, in washing/diluting buffer, are added to each well and incubated on a shaker for a sufficient time, preferably, 1 hour, at room temperature. The strips are then washed several times, e.g., four times, in a washing/diluting buffer. Secondary antibodies, preferably rabbit anti-goat peroxidase labeled antibodies (ICN), diluted, preferably 1 :1000, in washing/diluting buffer, are added to each well and incubated on a shaker for a sufficient time, preferably, 1 hour, at room temperature. The strips are washed again, e.g., four times, in washing/diluting buffer, and developed in a substrate solution, e.g. 2 ml of TMB (3,3'5,5'-Tetramethylbenzidine) solution. Insoluble colored bands will develop at the sites on the test strip occupied by antibodies. The reaction is stopped by replacing the substrate solution with a quenching reagent, e.g., distilled water. The strips are then read, dried, and mounted for further analysis.

According to the present invention, both IgG and IgE anti-Parvovirus B19 antibodies exist in serum of parvovirus infected patients. However, while the total IgG immunoglobulin level remains almost unchanged before and after parvovirus infection, it has now been discovered that the total IgE immunoglobulin level of a subject increases significantly after exposure to parvovirus. One of the most remarkable discoveries of the present invention is the recognition of long-term persistence of IgE anti-Parvovirus B19 antibodies, as well as a significant decrease in levels of total serum IgE immunoglobulin during the same term, e.g., 210 days post-symptom presentation ("psp"). This result demonstrates that there is an IgE-specific memory component in a parvovirus infection, particularly, a Parvovirus B19 infection.

As detailed herein, the total IgE immunoglobulin in a normal subject has a level ranging from 20 to 100 IU/ml for a minor subject (Pellegrino et al. supra) or 42-167 IU/ml for an adult subject (Henry J. B. ed., *Clinical Diagnosis and Management by Laboratory Methods,* 20th Ed., at 1429, Saunders Publishing, 2001), and does not contain detectable levels of IgE anti-Parvovirus B19 antibodies. In accordance with the present invention, a subject is diagnosed as having a parvovirus infection, particularly, Parvovirus B19 infection, when IgE anti-Parvovirus B19 antibodies are present in the sample in detectable amounts from the subject.

In another aspect of the present invention, the detection of IgE anti-Parvovirus B19 antibodies permits the prognosis of a subject having a parvovirus infection, particularly a Parvovirus B19 infection, by stratifying the subject, particularly based on signs, symptoms, severity, duration, co-morbid factors, and long-term sequelae of the infection, preferably by further directing treatment options for the subject. That is, in accordance with the present invention, the detection of IgE anti-parvovirus B19 antibodies can serve as a marker of arthropathies, aplastic anemia, hydrops fetalis and/or cardiomyopathies.

By "diagnosis", "diagnosing", "diagnostic" or "detecting" is meant an act or process of identifying or determining the presence, nature and cause of a pathological condition, such as a parvovirus infection or other infections, through evaluation of patient history, examination and review of the presence of IgE anti-Parvovirus B19 antibodies and/or the level of total IgE immunoglobulin in a patient.

By "prognosis" or "prognostic" is meant predicting the probable course, outcome, and likelihood of recovery from a pathological condition, such as a parvovirus infection or other infections, and particularly, can be useful to direct future treatment options.

A "subject" in accordance with the present methods can be any mammalian subject, including cows, dogs, cats, horses, humans, monkeys, and rabbits. A preferred subject is a human.

In a further aspect of the present invention, antigen specific IgE can be determined with a greater sensitivity by the detection method described. Traditional serological methods do not detect IgE antibodies in Parvovirus B19 infected patients. Therefore, the detection method of the present invention provides a greater degree of sensitivity than conventional serology, such as an ELISA method used in previous studies.

A test kit for use in detecting the presence of IgE anti-Parvovirus B19 antibodies is further contemplated by the present invention. The test kit comprises one or more of Parvovirus B19 antigens or antigen subfragments described above and at least one indicator which makes it possible to detect a complex of the antigen or antigen subfragment and an IgE antibody. A positive result will indicate the presence of IgE anti-Parvovirus B19 antibodies in a subject, thereby detecting a parvovirus infection in a subject.

Another embodiment of the present invention is directed to substantially pure IgE anti-viral antibodies and their use in treating diseases caused by, or resulting from or associated with infections by the underlying viruses.

By the term "substantially pure", it is meant that the IgE antiviral antibodies is at least 70% pure by weight and is substantially free of other antibodies, i.e., additional antibodies comprise at most about 2% of the antibody by weight and more preferably less than about 1% by weight. It is more preferably at least about 85% pure by weight and most preferably at least 90% pure by weight.

Another embodiment of the present invention is directed to IgE anti-Parvovirus B19 antibodies and more specifically to substantially pure IgE anti-Parvovirus B19 antibodies.

The substantially purified, monoclonal and humanized anti-viral antibodies can be isolated using well-known techniques.

One aspect of the present application is directed to IgE anti-Parvovirus B19 monoclonal antibodies or humanized antibodies or human antibodies or substantially pure antibodies of the antibodies described herein. Monoclonal antibodies or humanized antibodies or human antibodies can be generated by well established techniques. For a general review, see, e.g., Little, et al., *Of mice and men: hybridoma and recombinant antibodies*, Immunology Today, 21:364-69,2000; Luiten et al., *Chimeric immunoglobulin E reactive with tumor-associated antigen activates human Fc epsilon RI bearing cells*, Hum Antibodies, 8(4):169-80, 1997; Schuurman et al., *Production of mouse/human chimeric IgG monoclonal antibody to the house dust mite allergen Der p2 and ites uses for the absolute quantification of allergen-specific IgE*, J Allergy Clin Immunol, 99(4):545-50,1997.

See, also Harlow and Lane, *Antibodies: A Laboratory Manual*, Cold Spring Harbor Laboratory, Cold Spring Harbor, N.Y. 1988. Although the latter reference provides techniques in the art for making IgG, the general techniques are also applicable for producing antibodies for IgE, which include production of monoclonal antibodies (See Harlow and Lane, p.148, 1988); production of antibody producing hybridomas (See Harlow and Lane, p.196, 1988) and purification of antibodies (See, Harlow and Lane, p.288, 1988). Conventional purification techniques for IgE antibodies in general can be used to purify anti-viral IgE antibodies. ,See for example, the purification for IgE antibodies from tissue culture, as described in the article by Ikeyama, et al., "IgE Fc fragment produced in mouse L calls", *Molecular Immunology* 1985; 24: 1039; and in sera as described by Pellegrino, et al., "HIV type1 -specific IgE in serum of long-term surviving children inhibits HIV-1 production, in vitro", *AIDS Research and Human Retroviruses*. 2002, 18,367-376, Kleine Tebbe, et al. "Purification of immunoglobulin (IgE) antibodies from sera with high IgE filters", *J. Imm. Meth.*, 1995, 179, 153-164; Rihet, et al. "Strong serum inhibition of specific IgE correlated to competing IgG4, revealed by a new methodology in subjects from a S. Mansoni endermic area", *Eur. L. Immuno.* 1992. 22, 2063-2070. In addition, techniques for the production of chimeric fusion IgE antiviral antibodies can be prepared using conventional techniques, such as described in Bendixsen, et al. "Development of a new monoclonal antibody to ovine chimeric IgE and its detection of systemic and local IgE antibody responses to the intestinal nematode Trichostrongylus colubriformis" *Vet Immunol Immunopathol.*, 2004;97:11-24; Krauss, et al., "Recombinant CD4-IgE, a novel hybrid molecule, inducing basophils to respond to human immunodeficiency virus (HIV) and HIV-infected target cells", *Eur J Immunol.*, 1995;25: 192-9; Ikeyama, "Purification and characterization of recombinant human IgE Fc fragment produced in mouse L cells", *Molecular Immunology*, 1985; 24:1039. Humanized antibodies for IgE, as described in Furtado, et al., "The production and characterization of a chimaeric human IgE antibody, recognizing the major mite allergen Der p 1, and its chimaeric human IgG1 anti-idiotype", *Mol Pathol.*, 2002; 55:315-24 can also be utilized. The contents of all of the aforementioned publications are incorporated by reference.

The antibodies prepared can be further purified by conventional techniques known in the art.

Hybridoma cell lines which produce IgE anti-Parvovirus B19 form another embodiment of the present invention.

Another aspect of the present invention is directed to functional derivatives of the monoclonal or humanized antibodies of the present invention.

"Functional derivatives" refer to antibody molecules or fragments thereof which are derived from IgE antiviral antibodies, for example, IgE anti-Parvovirus B19 antibodies and which have retained the antigenic specificity and the functional activity (e.g., reactivity to Parvovirus B19 specific antigens) of the original IgE antiviral antibody. Examples of functional derivatives include Fab, Fab', F(ab')$_2$, single chain antibodies, and chimeric antibodies of IgE antiviral antibodies, such as IgE anti-Parvovirus B19 antibody and the like.

A further aspect of the invention is directed to pharmaceutical compositions which comprise a therapeutically effective amount of a substantially pure IgE antiviral antibody such as IgE anti-Parvovirus B19 antibodies and/or functional derivatives thereof and combinations thereof.

The pharmaceutical compositions of the present invention are associated with a pharmaceutically acceptable carrier. As used herein, a pharmaceutically acceptable carrier includes any and all solvents, including water, dispersion media, culture from cell media, isotonic agents and the like that are non-toxic to the host. Preferably, a pharmaceutically acceptable carrier is an aqueous isotonic buffered solution with a pH of around 7.0. The use of such media and agents in therapeutic compositions is well known in the art.

The pharmaceutical composition may additionally contain other ingredients typically used in pharmaceutical compositions, excipients, adjuvants, anti-microbial agents, isotonic agents, anti-oxidants, taste-masking agents, sweetening agents, dye and the like. In addition, the pharmaceutical composition may contain cyctokines, e.g., Th1, Th2, IL-1, IL-4 or IL-10.

According to the present invention, in addition to increased CD23 expression in peripheral blood and the presence of IgG and IgE anti-Parvovirus B19 antibodies in serum of the infected patient, other factors, such as Th1 and Th2 cytokines, can contribute to the immunopathogenesis of Parvovirus B19 infection. In the present invention, cytokine specific mRNA expression was compared on both day 0 and day 14 psp. Analysis of the cytokine pattern revealed a deviation of the cytokine profile Th2 -like (IL-2-, IFN-gamma-) on day 0, to Th1- like (IL-2+, IFN-gamma+) on day 14 psp. Without intending to be limited to any particular theory, it is believed that during early viral infection, parvovirus suppresses certain Th1-type cell responses, including IL-2 production, and parvovirus gene products are involved in suppressing host immune responses and T cell activation. The presence of IFN-γ on day 14 psp indicates that IFN-γ operates as a final effector to activate anti-viral mechanism(s) within cells infected by parvovirus. The presence of these cytokines by day 14 psp indicates that certain cells are not activated during the early immune response and that the process of Th1/Th2 selection cannot begin until 10-14 days after exposure to the antigen (virus). It is further believed that IL-2 and IFN-γ expression on day 14 psp represents the addition of ah independent Th1 type cellular immunity required for efficient viral clearance.

In accordance with the present invention, the presence of antigen-specific IgE antibodies in serum represents a significant marker of viral responses. For example, the observation that IgE anti-Parvovirus B19 antibodies present when infection is first detected, and are still detectable seven months later, demonstrates that IgE anti-Parvovirus B19 antibodies not only represent a significant marker of viral responses but also play a major role in anti-viral immunity, believed to be in conjunction with CD23+ cells. Therefore, IgE anti-Parvovirus B19 is useful for a pharmaceutical composition.

An even further aspect of the invention is directed to methods of treating a subject suffering a pathological condition characterized by viral infection e.g., parvovirus infection, particularly, Parvovirus B19 infection. According to the present invention, the subject is treated by administering a therapeutically effective amount of a pharmaceutical composition of the present invention.

By "treating" is meant that the pathological conditions associated with parvovirus infection are inhibited, reduced, or eliminated, or the occurrence of the pathological conditions is prevented or delayed.

Pathological conditions which can be treated and/or diagnosed in accordance with the present invention include viral infections of subject. Examples of diseases which the IgE antiviral antibodies, especially substantially pure IgE antiviral antibodies can be used to treat include, but are not limited to, HIV, measles, mumps, rubella, parvovirus B19, RSV, SARS (coronavirus), West Nile virus, viral hemorrhagic fever, hepatitis viruses, such as HAV, HBV, HCV and the like; leukemia viruses, such as HTLV and the like; Herpes Simplex Virus, VZV, CMV, EBV (Epstein Barr Virus), encephalitis viruses, adenoviruses, rhinoviruses, rotaviruses, polio viruses, parainfluenza, influenza, Coxsackie viruses, rabies, Puumala, and the like. In an embodiment, for example, the pathological condition which can be treated in accordance with the present invention include parvovirus infection related aplastic anemia and/or fetal death in patients with sickle cell anemia, chronic arthropathies, chronic anemia, and cardiomyopathies.

The antibody used in the pharmaceutical composition is dependent upon the virus causing or associated with the disease or malady. Conventional means can be used to determine whether a disease is caused by or associated with a virus and the identification of the virus causing or associated with the malady. These methods include enzyme linked immunosorbent assay (ELISA), nucleic acid testing, western blot and the like. Once a virus is determined to be the cause or to be associated with the disease, the presence of specific IgE anti-virus antibodies is determined using the technique described herein by subjecting a sample such as plasma, peripheral blood, urine, sputum/saliva or serum to detection methods known in the art, such as western blot or enzyme linked immunosorbent assay, radioimmunoassay (RIA), and the like. X, for example, Bluth, et al., Detection of IgE anti-parvovirus B19 and increased CD23+ B cells in parvovirus B19 infection: relation to $TH_2$ cytokines, *Clinical Immunology.* 2003;108: 152-158, the contents of which are incorporated by reference.

In accordance with the present invention, an antibody or an antibody derivative can be combined with the carrier in any convenient and practical manner, e.g., by solution, suspension, emulsification, admixture, encapsulation, absorption and the like, and if necessary, by shaping the combined compositions into pellets or tablets. Such procedures are routine for those skilled in the art.

Dosages of an antibody or an antibody derivative to be therapeutically effective depend on the disease state and other clinical factors, such as age, weight and condition of the subject, the subject's response to the therapy, the type of formulations and the route of administration. The precise dosage of an antibody to be therapeutically effective can be determined by those skilled in the art. As a general rule, the therapeutically effective dosage of an antibody can be in the range of about 0.5μg to about 2 grams per unit dosage form, or preferably, about 0.5 μg to about 1 mg per unit dosage form. A unit dosage form refers to physically discrete units suited as unitary dosages for mammalian treatment: each unit containing a pre-determined quantity of the active material calculated to produce the desired therapeutic effect in association with any required pharmaceutical carrier. The methods of the present invention contemplate single as well as multiple administrations, given either simultaneously or over an extended period of time.

The administration of an antibody may be carried out in any convenient manner, including by aerosol inhalation, injection, ingestion, transfusion, or implantation. Preferably, the antibodies of the present invention are administered to a patient by injection, and more preferably subcutaneous (s.c.), intraperitoneal (i.p.), intra-arterial (i.a.), or intravenous (i.v.) injection.

Typically, treatment begins by administering doses less than the determined optimum dosage. The dosages may be increased incrementally until the desired treatment affect is achieved. In an exemplary embodiment wherein treatment is administered intravenously or intramuscularly, dosage is determined based on the body weight of the patient. The amount administered is a therapeutically effective amount. Preferably, the treatment is administered to the patient in a dosage amount of between about one picogram (pg) per kilogram (kg) per day (d) (pg/kg/d) to about three grams (g) per kg per d (g/kg/d), wherein the kg value represents the weight of the patient. In another embodiment, the solution is administered to the patient in a dosage amount of between about 75 micrograms (μg) per kg per d (μg/kg/d) to about 400 milligrams (mg) per kg per d (mg/kg/d). Treatment can administer for up to about seven days, although the treatment time may vary depending on factors such as the dosage, the condition and age of the patient, severity of the disease caused by, resulting from or associated with the virus infection, and the like. As indicated hereinabove, the precise dosage to be therapeutically effective can be determined by one of ordinary skill in the art. Treatment may be repeated every about one to about six months from the initial treatment.

For treatments being administered intravenously or intramuscularly, the solutions must be prepared in a suitable, injectable and sterile, form. Suitable injectable forms include, but are not limited to, aqueous solutions and dispersions prepared in carriers such as water, ethanol, glycerol, propylene glycol, liquid polyethylene glycol, vegetable oils, and the like. Further, the solutions should be prepared and stored in a sterile form and be adequately protected against contamination by microorganisms, such as fungi, bacteria and viruses. Contamination may be prevented by the use of antimicrobial agents such as parabens, chlorobutanol, phenol, sorbic acid, thimerosal, and the like.

In another exemplary embodiment, the IgE antiviral antibody, especially substantially pure antiviral antibody is administered to the patient as an inhalant. The inhalant may be in the form of an aerosol. Administration as an inhalant allows for the direct treatment of areas of the respiratory tract. It may also provide a more direct or efficacious route of said invention into the bloodstream. Thus, administering said invention in the form of an inhalant is useful for, but not limited to, the treatment of respiratory disorders or diseases, for example, asthma and asthma-related conditions.

In the embodiment wherein the IgE antiviral antibody or substantially pure antibody is administered as an inhalant, it should be contained in, or formed into, particles of a size sufficiently small to pass through the mouth and larynx upon inhalation and into the bronchi and alveoli of the lungs. The particles should have a size in the range of about one to about ten microns in diameter.

In a further exemplary embodiment, IgE antiviral antibody of the present invention, especially substantially pure antibody of the present invention, as defined herein, is administered to the patient topically. Topical applications are particularly useful for direct localized treatment. Topical applications may include the application of topical treatments, including but not limited to, ointments, creams, transdermal patches, as well as any combination of the foregoing topical treatments. Ointments or creams may be prepared comprising a therapeutically effective amount of IgE antiviral antibody, especially substantially pure IgE antiviral antibody, a suitable ointment or cream delivery medium. The ointment or cream may be applied to the areas of the patient requiring the treatment. The composition contained in the ointment or cream win diffuse transdermally into the body of the patient providing treatment to the effected area.

Additionally, as mentioned above, the IgE antiviral antibody, especially substantially pure IgE antiviral antibody, of the present invention can be administered using a transdermal patch. The transdermal patch may be worn on the skin of the patient like a bandage. The transdermal patch allows for a prolonged treatment to be administered. For example, the patient may wear the transdermal patch for a plurality of hours and receive low dose treatments throughout that period. Other applicable treatment methods may be used in accordance with the teachings of the present invention. For example, a solution comprising said IgE antiviral antibody, especially substantially pure IgE antiviral antibody, of the present invention may be injected subcutaneously.

The foregoing techniques are provided merely as exemplary methodologies for administering treatment to a patient and it is to be understood that the teachings of the present invention are generally applicable to any suitable methodology and should not be limited to any particular techniques described herein.

All the publications mentioned in the present disclosure are incorporated herein by reference. The terms and expressions which have been employed in the present disclosure are used as terms of description and not of limitation, and there is no intention in the use of such terms and expressions of excluding any equivalents of the features shown and described or portions thereof, it being recognized that various modifications are possible within the scope of the invention.

Unless indicated to the contrary, the plural denotes the singular and vice versa. Moreover, unless indicated otherwise, percentages are by dry weight.

The present invention is further illustrated by the following specific examples which are not intended in any way to limit the scope of the invention.

EXAMPLE 1

Patient Specimens

Peripheral blood (5 ml total) was obtained from a pediatric Parvovirus (B19) patient (male, 8 yrs. old, Caucasian), with an elevated serum IgE level (>100 IU/ml). Patient had positive skin prick to various allergens, including tree and grass pollens and ragweed. Parvovirus B19 infection was established by: (1) EIA and (2) positive pattern on Western blots. Patient presented with a "slap cheek" rash over his face, and a diffuse erythematous rash over his neck, ears, hands, elbows, knees, and complained of achy joints.

Clinical Diagnosis of Parvovirus B19

Clinical symptoms of Parvovirus B19 patient included "slap cheek," rash over facial area, diffuse erythematous rash over body regions (neck, ears, hands, elbows, knees), and arthralgias. (Table I)

TABLE I*

| CLINICAL DIAGNOSIS OF PARVOVIRUS B19 |
| --- |
| Signs and Symptoms: |
| "Slap Cheek" appearance<br>erythamatous rash on ear, neck, elbows, knees<br>arthralgias |
| Diagnostic tests |
| EIA (Parvovirus IgM & IgG)[a]<br>Western Blot[b] |

*Presentation of Parvovirus B19 infection in an 8 year old patient.
[a]Day 0: Parvovirus B19 Ab (IgM, IgG): 1.0, 3.7 units, respectively (reference range 0.00–0.89). Data expressed as ratio report. Day 14: Parvovirus B19 Ab (IgM, IgG): 0.5, 3.0 units, respectively (reference range 0.00–0.89). Data expressed as ratio report.
[b]Days 0 and 14: IgE anti-Parvovirus B19 Ab present

EXAMPLE 2

Blood

For studies of serum immunoglobulins (Ig), blood was collected into red top MONOJECT™ tubes (Sherwood Medical, St. Louis, Mo.) and sent to Quest Diagnostics Incorporated (Teterboro, N.J.) for Ig determinations.

For studies of surface markers, blood was collected into EDTA MONOJECT™ tubes (Sherwood Medical) and stored at room temperature for up to 2 hrs when complete blood counts were performed (Sysmex, McGraw Park, Ill.); flow microfluorimetry studies (Coulter Epics XL/MCL) (Beckman Coulter, Miami, Fla.) were performed within 3 hrs.

TABLE II*

IMMUNOGLOBULIN LEVELS IN SERUM OF PARVOVIRUS B19 PATIENT

| | Immunoglobulin | | | | | | |
|---|---|---|---|---|---|---|---|
| Day | IgM (mg/dl) | IgG$_1$ (mg/dl) | IgG$_2$ (mg/dl) | IgG$_3$ (mg/dl) | IgG$_4$ (mg/dl) | IgA (mg/dl) | IgE (IU/ml) |
| 0 | 45 | 621 | 87 | 52 | 13 | 37 | 256 |
| 14 | 49 | 507 | 109 | 54 | 13 | 58 | 233 |

*Immunoglobulin levels in serum of Parvovirus B19 patient (nephelometry, Total IgE Fluoroenzymeimmunoassay), on days 0 and 14 psp, as determined by Quest Diagnostics. Data are expressed as either mg/dl or IU/ml.

scale. Specific fluorescence was reported as the percentage of cells with relative fluorescence intensity scored above background. The total numbers of lymphocytes were calculated from the white blood cell (WBC) count. Data are expressed as total lymphocytes/mm$^3$.

Distributions of blood lymphocyte subpopulations.

On days 0, 14, and 210 psp distributions of lymphocyte subpoulations in peripheral blood of the same Parvovirus B19 patient were determined. On days 0-210 psp, there was virtually no change in total numbers of T cells (CD3+CD4+, CD3+CD8+, CD45 RA, and CD45RO) and NK precursor cells (CD3/16+56+) (Table III). In contrast, total numbers of both CD23- CD19+ and CD23+CD19+ B cells increased on day 14 psp (17 and 93%, respectively). On day 210 psp, total numbers of CD23-CD19+ B cells further increased (86%), and CD23+CD19+ B cells remained unchanged to those of day 14 psp (Table III).

TABLE III*

DISTRIBUTIONS OF LYMPHOCYTE SUBPOPULATIONS IN PERIPHERAL BLOOD OF PARVOVIRUS B19 PATIENT

| | CD3+CD4+ | | CD3+CD8+ | | CD16+56+ | | CD45RA+ | | CD45RO+ | |
|---|---|---|---|---|---|---|---|---|---|---|
| Day | mm$^3$ | (%) | mm$^3$ | (%) | mm$^3$ | (%) | mm$^3$ | (%) | mm$^3$ | (%) |
| 0 | 703 | 50 | 419 | 30 | 64 | 5 | 1014 | 72 | 724 | 52 |
| 14 | 859 | 47 | 548 | 30 | 92 | 5 | 1113 | 61 | 910 | 50 |
| 210 | 1080 | 45 | 768 | 32 | 72 | 3 | 1584 | 66 | 1008 | 42 |

*The distributions of lymphocyte subpopulations in peripheral blood of a representative Parvovirus B19 patient was determined on days 0, 14, and 210 post symptom presentation (psp), by flow microfluorimetry (Coulter Epics XL/MCL). Data are expressed as mean total cells/mm$^3$ or mean percentage (%) of positive cells.

EXAMPLE 3

Determination of Cell Surface Markers

Antibodies.

Mouse anti-human monoclonal antibodies (mAbs) which were directly conjugated to fluorescein isothiocyanate (FITC): CD45, CD45RA, CD23, Simultest CD3/CD4, Simultest CD3/CD8, Simultest CD3/CD19, and CD3/CD16+CD56.

Mouse anti-human mAbs which were directly conjugated to phycoerythrin (PE): CD45RO.

All mAbs and appropriately matched isotype controls were purchased from Becton Dickinson BioSciences (San Jose, Calif.), and titrated to obtain maximum staining efficiency according to manufacturer's recommendation.

Immunofluorescence Assay.

Peripheral blood (100 ul) was incubated with conjugated antibodies for 10 min at room temperature. Erythrocytes were lysed with whole blood lysing solution (ImmunoPrep®) (Beckman Coulter). Flow cytometric analysis was performed on a Coulter Epics® XL/MCL Flow Cytometer using System II software (Coulter) and CytoComp (Coulter). Forward and side scatter were used to identify the lymphocyte population and CD45 was used to establish an optimal lymphocyte gate. A minimum of 15,000 events were collected. The gain on the photomultiplier tube detecting fluorescence intensity was adjusted so that 99% of cells with background fluorescence staining were scored between $10^0$ and $10^1$ on a 4-decade log

EXAMPLE 4

Total Serum Immunoglobulins.

Total serum immunoglobulins (IgM, IgG, and IgA) were determined by Quest Diagnostics Incorporated (Teterboro, N.J.), using nephelometry, which was performed according to standard procedure. The results were expressed in mg/dL (reference range for healthy child serum: IgM: 60-263 mg/dL; IgG: 694-1618 mg/dL; IgA: 69-378 mg/dL). Total serum IgE levels were detected by the UniCAP™ Total IgE Fluoroenzymeimmunoassay (Pharmacia & Upjohn Diagnostics, Kalamazoo, Mich.) which was performed according to manufacturer's recommendation. Data are expressed as IU/mL (reference range for healthy child serum: IgE: 20-100 IU/ml; reference range for healthy adult serum: 42-167 IU/ml or 100-400 ng/ml; 1 IU=2.4 ng (Henry ed.)).

Serum Immunoglobulins.

a. Total IgM, IgG, IgA. Serum obtained from Parvovirus B19 infected patient contained similar levels of total Ig, IgG, IgA on days 0 and 14 (Table II); these levels were within normal range (see above).

b. Total IgE. Serum obtained from Parvovirus B19 infected patient contained total serum IgE levels which increased from 150 IU/mL before infection, to 256 IU/mL on day 0, and was 233 IU/mL on day 14 psp, then returning to pre-infection levels on day 210 psp, but were still elevated above the normal range (>100 IU/mL) (7) (Total IgE fluoroenzymeimmunoassay) (FIG. 1).

EXAMPLE 5

Parvovirus B19 Serum Antibody Detection.
  a. IgM and IgG. Serum IgM and IgG antibodies to Parvovirus B19 were determined by enzyme immunoassay (EIA) performed by Quest Diagnostics (Teterboro, N.J.), according to the standard procedure. Data were reported as a ratio report.
  b. IgE. Parvovirus B19 Western blot strips (Mikrogen, Martinsried, Germany) were incubated with sera diluted 1:100 in washing/diluting buffer (Tris-buffered saline, NaCl, Tween-20, 0.01% MIT, 0.1% oxypyrion, protein) on a shaker for 20 hr at room temperature. The strips were washed four times in washing/diluting buffer. Goat polyclonal anti-human IgE (ICN Biomedicals, Aurora, Ohio), diluted 1:50 or 1:100 in wash buffer, was added to each well and incubated on a shaker for 1 hr at room temperature. The strips were washed four times in wash buffer. Rabbit anti-goat peroxidase labeled antibody (ICN), diluted 1:1000 in washing/diluting buffer, was added to each well and incubated on a shaker for 1 hr at room temperature. The strips were washed again four times in washing/diluting buffer, and developed in 2 ml of a TMB substrate solution. The reaction was stopped by replacing TMB solution with distilled water. The strips were then read, dried, and mounted. In addition, IgG anti-Parvovirus B19 Western blot (Mikrogen) was determined according to manufacturer's recommendation.

Result
  Anti-Parvovirus B19 Abs:
  IgM & IgG. Serum obtained from Parvovirus B19 infected patient was assayed for the presence of serum anti-Parvovirus B19 Abs (IgM and IgG), in order to confirm diagnosis of Parvovirus B19 infection in patient (EIA) (Table I). On Day 0 Parvovirus B19 Abs (IgM, IgG) were 1.0 and 3.7 units, respectively. However, by day 14, Parvovirus B19 Abs (IgM, IgG) decreased to 0.5 and 3.0 units, respectively. Reference range (IgM, IgG): 0.000-0.89. Data are reported as ratio report.

Figure 2:
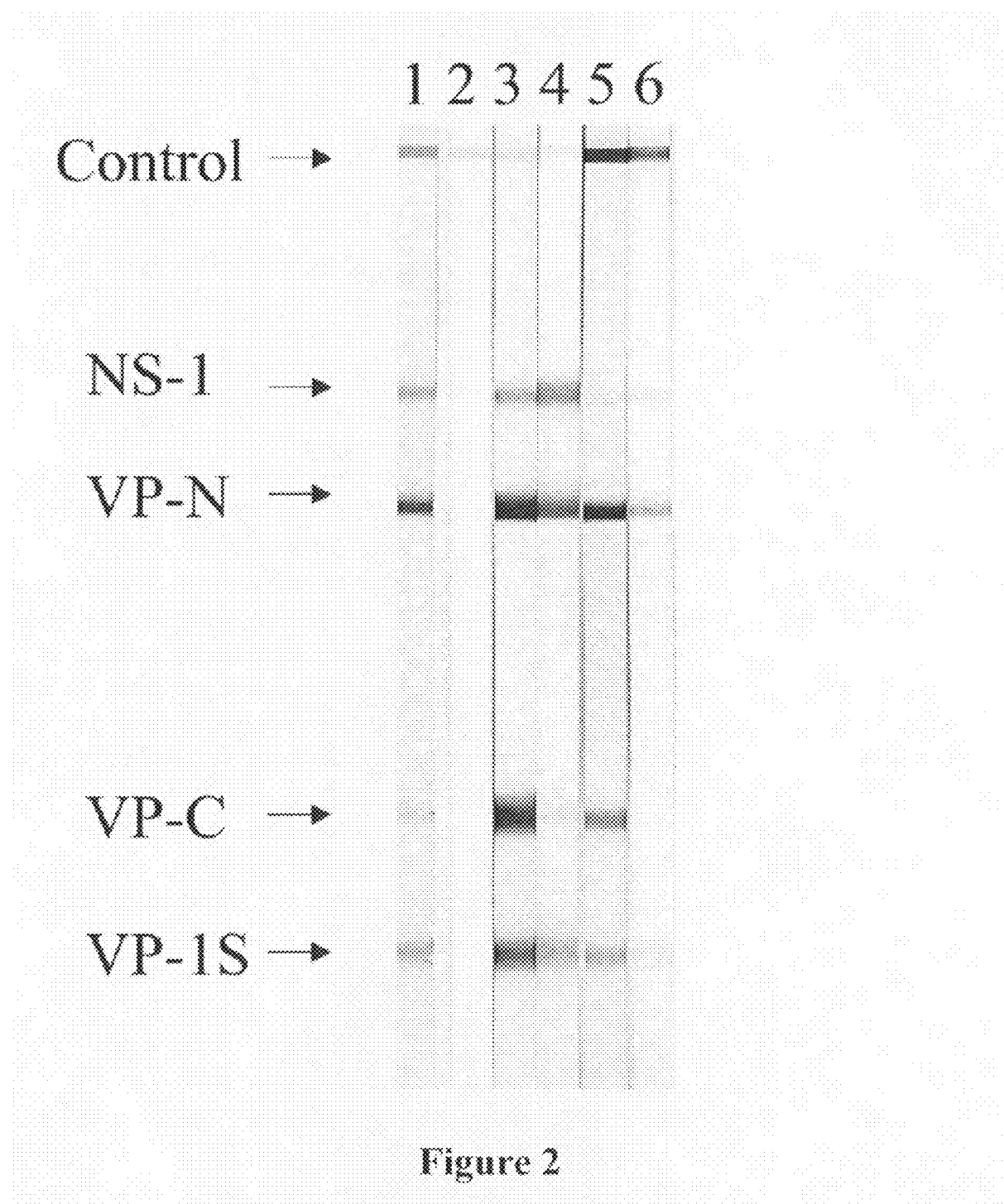
FIG. 2 depicts Western blot analysis of anti-Parvovirus B19 antibodies. Serum was incubated with Western blot strips containing Parvovirus B19 antigens NS-1, VP-N, VP-C and VP-1S. Lane 1: control strip showing representative bands. Lane 2: serum from a Parvovirus B19 negative donor. Lane 3: patient serum incubated with anti-human IgG (1:1000). Lane 4: patient serum incubated with anti-human IgE (1:100). Lane 5: patient serum incubated with anti-human IgG (1:1000) on day 210 psp. Lane 6: patient serum incubated with anti-human IgE (1:100) on day 210psp. Results did not differ between days 0 and 14 psp (Lanes 3 and 4). Control band represents anti-human immunoglobulin. The relative serum concentration of IgE compared with IgG is 1:1-100 million.

IgE anti-Parvovirus B19:
  Serum obtained from the Parvovirus B19 infected patient serum contained IgG anti-Parvovirus B19 antibodies on days 0-2 10 psp as determined by EIA and also by Western blot (FIG. 2, lane 3),. Further, patient serum also contained antigen-specific IgE directed against Parvovirus B19 component VP-N (FIG. 2, lane 4). Western blot analysis also revealed faint bands representing IgE anti-NS-1, VP-1S, and VP-C (data not shown). Interestingly, on day 210 psp, patient serum contained both IgG and IgE anti-Parvovirus B19 antibodies directed against VP-N and VP-1S (FIG. 2, lanes 5 and 6, respectively), and a faint band representing IgG anti-NS-1 (FIG. 2, lane 5). In contrast, serum of Parvovirus B19 negative donor did not contain either IgG or IgE anti- NS-1, VP-N, VP-C, or VP-1S antigens (FIG. 2, lane 2).

EXAMPLE 6

Cytokine Specific mRNA
  RNA extraction and polymerase chain reaction (PCR).
  Total cellular RNA (2 μg/mL) was extracted from peripheral blood mononuclear cells ("PBMC") as previously described (Chomczynski et al., *Anal Biochem.* 162: 156-66, 1987), using Trizol Reagent (GIBCO/BRL), according to manufacturer's recommendation. Pellets were dissolved in TE buffer (10 mM Tris HCl (Sigma, St. Louis, Mo.), pH 7.5, 1 mM EDTA, Sigma), and stored at −70° C. in a Bio-Freezer (Forma Scientific, Marietta, Ohio). Expression of interleukin-2 (IL-2), interleukin-4 (IL-4), interleukin-6 (IL-6), interleukin- 10 (IL-10), and interferon-gamma (IFN-γ) mRNA was determined using the Advantage® One-Step RT-PCR Kit (Clontech, Palo Alto, Calif.), according to manufacturer's recommendation. PCR was conducted using primer pairs specific for IL-2, IL-4, IL-6, IL-10, and IFN-γ (Expected band sizes: 305, 344, 628, 328, and 427 basepairs (bp), respectively). A beta-actin primer set was used as an internal positive control. Negative controls, consisting of water (no DNA), but addition of primers, were included in every experiment. The PCR amplicons were separated by electrophoresis in a 1.8% agarose (Seakem LE) gel (FMC, Rockland, ME), and visualized with ethidium bromide (Sigma).

Cytokine Expression by PBMC
  On day 0, patient's PBMC expressed mRNA for the Th$_2$ cytokines IL-4 and IL-10, but not for the Th$_1$ cytokines IFN-γ or IL-2. However, by day 14, PBMC expressed mRNA for the Th$_1$ cytokines IFN-γ and IL-2, as well as IL-4 and IL-10. PBMC did not express mRNA for IL-6 at either time point (Table IV).

TABLE IV*

SUMMARY OF CYTOKINE PRODUCTION BY PERIPHERAL BLOOD MONONUCLEAR CELLS (PBMC) FROM PARVOVIRUS B19 PATIENT

| | Cytokines | | | | |
| --- | --- | --- | --- | --- | --- |
| | Th-1 | | Th-2 | | |
| Day | IL-2 | IFN-γ | IL-4 | IL-6 | IL-10 |
| 0 | − | − | + | − | + |
| 14 | + | + | + | − | + |

*Unfractionated PBMC from representative Parvovirus B19 patient was evaluated for the presence (+) or absence (−) of Th1 type (IL-2, IFN-γ) cytokines and Th2 type (IL-4, IL-6, IL-10) cytokines on day 0 and 14 p.i. Expression of cytokine-specific mRNA production was determined by Advantage One-Step RT-PCR (Clontech), as described in materials and methods.

What is claimed is:

1. A method for diagnosing a subject suffering from parvovirus infection, comprising detecting the presence of IgE anti-Parvovirus B19 antibodies in a biological sample from said subject.

2. The method of claim 1, wherein said detection step is performed by Western blot or ELISA.

3. The method of claim 1, wherein said biological sample is serum.

4. The method of claim 1, wherein said biological sample is plasma.

5. The method of claim 1, wherein said biological sample is peripheral blood.

6. A method for diagnosing a subject suffering from parvovirus infection, comprising detecting the presence of IgE anti-Parvovirus B19 antibodies in said subject and stratifying said subject based on signs, symptoms, severity, duration, co-morbid factors, and long-term sequelae of a Parvovirus B19 infection.

7. A test kit for use in detecting the presence of IgE anti-Parvovirus B19 antibodies, said test kit comprising:
  A) a Parvovirus B19 antigen or antigen subfragment
  B) at least one indicator to detect a complex of said antigen or antigen subfragment and an IgE antibody.

8. The test kit according claim 7, wherein said kit is a Western blot kit.

9. The test kit according claim 7, wherein said kit is a ELISA kit.

10. The test kit according claim 7, wherein said Parvovirus B19 antigen is selected from the group consisting of VP1, VP-2 and NS-1.

11. The test kit according claim 7, wherein said Parvovirus B19 antigen subfragment is selected from the group consisting of VP-1S, VP-N and VP-C.

* * * * *